United States Patent [19]

Moschner et al.

[11] Patent Number: 6,143,795
[45] Date of Patent: Nov. 7, 2000

[54] STABLE MITOXANTRONE SOLUTIONS

[75] Inventors: Katrin Moschner; Mario Weingart, both of Dresden; Michael Pieroth, Weinböhla; Wolfgang Morick, Dresden; Elisabeth Wolf-Heuss, Mosbach, all of Germany

[73] Assignee: Arzneimittelwerk Dresden GmbH, Germany

[21] Appl. No.: 09/299,131

[22] Filed: Apr. 26, 1999

[30] Foreign Application Priority Data

Apr. 27, 1998 [DE] Germany .......................... 198 18 802

[51] Int. Cl.⁷ .................................................. A61K 31/135
[52] U.S. Cl. .................................................. 514/656
[58] Field of Search ................................. 514/656

[56] References Cited

FOREIGN PATENT DOCUMENTS 0236822  9/1987  European Pat. Off. ............... 514/656

OTHER PUBLICATIONS

Dalton–Bunnow, Am. J. of Hospital Pharmacy, vol. 42, pp. 2220–2226, Oct. 1985.

Wang et al., Drug Development And Industrial Pharacy, 20(11), 1895–1903, 1994.

*Primary Examiner*—Jerome D. Goldberg
*Attorney, Agent, or Firm*—Gabriel P. Katona L.L.P.

[57] ABSTRACT

An aqueous solution of from about 1 mg/ml to about 5 mg/ml mitoxantrone.HCl, from about 0.01% wt. to about 0.15% wt. based on the solution of sodium edetate, sodium chloride, sodium acetate, and acetic acid, and a process for preparing the same.

5 Claims, No Drawings

STABLE MITOXANTRONE SOLUTIONS

FIELD OF THE INVENTION

The present invention relates to mitoxantrone solutions which, in addition to the active compound mitoxantrone (1,4-dihydroxy-5, 8-bis[[2-[(2-hydroxyethyl)amino]ethyl)-amino]9,10-anthraquinone, or its dihydrochloride salt known as novantrone, contain a stabilizer and are free of sulfite compounds, and the use of these solutions for injection and as an infusion solution concentrate.

BACKGROUND

The dihydrochloride salt of mitoxantrone is an anthraquinone derivative having the chemical name 1,4-dihydroxy-5, 8-bis[[2-[(2-hydroxyethyl)amino]ethyl]-amino]9,10-anthraquinone or its hydrochloride of the formula

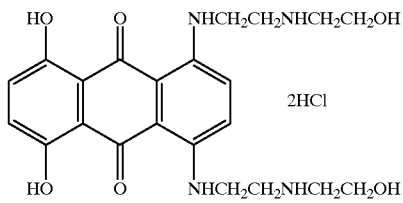

Empirical formula: $C_{22}H_{28}N_4O_6 \cdot 2$ HCl

Mitoxantrone or its salt novantrone exhibit antineoplastic, antiviral, antiprotozoal and immunomodulating properties. The compound is of great benefit as a cytostatic, in particular in the therapy of carcinoma of the breast, malignant lymphomas, acute leukemias, primary liver cell carcinoma and ovarian carcinoma.

Aqueous solutions of this compound have gained acceptance as a pharmaceutical formulation. The stability of mitoxantrone in aqueous solution is, however, quite limited. The compound is subject to oxidative decomposition if measures are not taken to slow this degradation or, better yet, to prevent it. Metal ions in particular, even in very low concentrations, can be used to increase this trend. This degradation can also be counteracted by the use of antioxidants.

European patent No. B-0 236,822 describes a preparation which is stabilized by a combination of a sodium metabisulphite, antioxidant at a specific pH, and disodium edetate as chelating agent, and glycine. Although this preparation is stable, it is unsatisfactory due to side effects of the additives. The use of sodium metabisulphite is disadvantageous even if it is very effective as a stabilizer.

Mitoxantrone solutions are commercially available. With a sulfite additive hypersensitivity reactions with in some cases serious side effects have been reported in man. When using preparations which contain sulfite in the concentrations customarily employed, life-threatening complications have been mentioned in the case of asthmatics with sulfite sensitivity.

The use of a metal ion-binding combination of at least two chelating agents represent additional constituents for such preparations.

A strongly acidic pH of less than 3 also has a disadvantageous effect, both on the tolerability and on the stability of the solutions, as reported by Wang, Da-Peng; Liang, Gow-Zaw; Tu, Yu-Hsing; Stability of mitoxantrone hydrochloride in solution, Drug Development and Industrial Pharmacy, 20(11), 1895–1903 (1994).

DESCRIPTION OF THE INVENTION

The object of the present invention is to provide an aqueous preparation which is free of sulfites, avoids the known side effects, and is stable over a relatively long period under normal storage conditions and also at an elevated temperature of 30° C.

In contrast to European patent No. B-0 236,822 it was surprisingly found that even sodium edetate alone is sufficient to stabilize mitoxantrone in aqueous solutions.

Accordingly, the invention comprises an aqueous solution of from about 1 to about 5 mg/ml mitoxantrone or its hydrochloride with from about 0.001 to about 0.15% wt sodium edetate, sodium chloride, sodium acetate and acetic acid at a pH of from about 3.0 to about 4.5.

Most suitably the sodium edetate is present in an amount of about 0.04% wt.

The solution of the present invention can be used as an injectable solution, and as a chemotherapeutic infusion solution concentrate for the treatment of the aforementioned cancers. It avoids the known side effects and has the stability required of pharmaceutical preparations.

In preparing the solution, the auxiliary ingredients sodium chloride and sodium acetate, acetic acid and sodium edetate are dissolved in water with suitably low oxygen content. The mitoxantrone hydrochloride is dissolved in one part of this solution. This active compound containing solution is added to the remaining part of the solution of the auxiliary ingredients and is made up to the final volume suitably with low-oxygen water containing suitably less than 0.6 ppm $O_2$, or maximum 7% of the amount required for $O_2$ saturation. The resulting solution is filtered and then dispensed into presterilized injection ampoules or vials, sealed and/or crimp-capped.

Conventional germproof filters are used for sterilization, such as, for example, membrane filters having a pore size of 0.2 μm. The water that is employed must be sterile and pyrogen-free according to the requirements of e.g. the European Pharmacopoeia 1997. The injection vials are suitably e.g. of Glass Type I according to the requirements of the European Pharmacopoeia 1997.

Suitably between from about 2.5 ml and about 50 ml per vial most suitably between 5 ml and about 15 ml per vial are filled. The amount of mitoxantrone per vial is from about 5 to about 100 mg, suitably from about 10 mg to about 30 mg. The vials are adequately flushed to remove the oxygen, when dispensing the injection solution under aseptic conditions, sealed with injection stoppers and crimp-capped.

The following example illustrates the invention in greater detail.

Injection Vial Containing About 5 ml of an About 0.2% Mitoxantrone Injection Solution

| Composition | |
|---|---|
| 1 ml of injection solution contains: | |
| mitoxantrone hydrochloride | 2.328 mg |
| sodium chloride | 8.000 mg |
| sodium acetate.3H$_2$O | 0.085 mg |
| disodium edetate | 0.040 mg |
| 1N acetic acid | 7.680 μl |
| Water q.s. | 1 ml |

Preparation of the Solution

In preparing the injection solution, sodium chloride, sodium acetate, acetic acid and disodium edetate are dissolved in the water of which the oxygen content was previously reduced. The solution is subdivided into two parts and mitoxantrone hydrochloride is dissolved in one part, which is mixed with the other part of the solution and made up to the final volume with water of suitably low oxygen contents and then the solution is sterilized by filtration through a membrane filter.

A vial containing about 12.5 ml of an about 0.2% wt injectable mitoxantrone solution of the example showed the following:

| Material | Storage temp. ° C. | Sum of the impurities in % wt. | | | |
|---|---|---|---|---|---|
| | | At start | After 6 months | After 18 months | After 24 months |
| Example | 25 | 0.60 | 0.75 | 0.72 | 1.39 |
| without sodium editate | 25 | 0.52 | 0.57 | 1.73 | 2.3 |
| Example | 30 | 0.60 | 0.82 | 1.78 | 2.00 |
| without sodium editate | 30 | 0.52 | 0.93 | 2.74 | 4.16 |
| Example | 40 | 0.60 | 1.45 | — | — |
| without sodium edetate | 40 | 0.52 | 2.72 | — | — |

We claim:

1. An aqueous solution which is free of sulfites and comprises a concentration of from about 1 mg/ml to about 5 mg/ml mitoxantrone.HCl, of from about 0.001% wt. to about 0.15% wt. based on the solution of sodium edetate, and further sodium chloride, sodium acetate, and acetic acid.

2. The aqueous solution of claim 1, wherein the concentration of said sodium edetate is about 0.04% wt.

3. A process for preparing the aqueous solution of claim 1, which comprises dissolving said sodium chloride, sodium acetate, acetic acid, and sodium edetate in water having a low oxygen content, dividing said solution into two parts, dissolving said mitoxantrone in one of said parts of said solution, combining said two parts, and adjusting the amount of the water to obtain said mitoxantrone and sodium edetate concentrations.

4. The process of claim 3, wherein the concentration of sodium edetate is about 0.04% wt.

5. An antineoplastic treatment process, which comprises administering to a patient in need therefor the aqueous solution of claim 1.

* * * * *